United States Patent [19]
Kourides et al.

[11] Patent Number: 6,114,144
[45] Date of Patent: *Sep. 5, 2000

[54] ISOLATION OF A GENE ENCODING HUMAN THYROTROPIN β SUBUNIT

[75] Inventors: Ione A. Kourides, Forest Hills; Graham Kerr Whitfield, New York, both of N.Y.

[73] Assignee: Sloan-Kettering Institute for Cancer Research, New York, N.Y.

[ * ] Notice: This patent is subject to a terminal disclaimer.

[21] Appl. No.: 08/957,545

[22] Filed: Oct. 24, 1997

Related U.S. Application Data

[63] Continuation of application No. 08/006,208, Jan. 9, 1993, Pat. No. 5,840,566, which is a continuation of application No. 07/671,134, Mar. 18, 1991, abandoned, which is a continuation of application No. 06/808,004, Dec. 11, 1985, abandoned.

[51] Int. Cl.[7] .............................. C12P 21/02; C12N 5/10
[52] U.S. Cl. ..................... 435/69.4; 435/320.1; 435/325; 435/252.3; 435/455; 435/471; 435/476
[58] Field of Search .................................. 435/69.1, 69.4, 435/320.1, 325, 252.3, 455, 471, 476

[56] References Cited

PUBLICATIONS

Shome, B. And A.F. Parlow (1973). The primary structure of the hormone–specific, beta subunit of human pituitary luteinizing hormone (hLH). *J. Clin. Endocrinol. Metab.* 36:618–621 (Exhibit 1);.
Talmadge, K. et al. (1983). The human genome contains seven genes for the β–subunit of chorionic gonadotropin put only one gene for the β–subunit of luteinizing hormone. 2: 281–289 (Exhibit 2).
Birken, Steven and Canfield, Robert E., *J. Biol. Chem.*, vol. 252, No. 15, pp. 5386–5397, 1977.
Boothby, Mark et al., *J. Biol. Chem.*, vol. 256, No. 10, pp. 5121–5127, 1981.
Croyle, Michelle L. and Maurer, Richard A., *DNA*, vol. 3, No. 4, pp. 231–236, 1984.
Fiddes et al., *J. Mol. Appl. Genet.* 1: 3–18, 1981.
Gurr, James A., et al., *Proc. Natl. Acad. Sci.*, vol. 80, pp. 2122–2126, 1983.
Hayashikaki et al., *FEBS Lett.* 188: 394–400, 1985.
Kaufman et al., *Molecular and Cell. Bio.* 2:1304–1309, 1982.
Keutmann, Henry T. and Williams, Roberta M., *J. Biol. Chem*, vol. 252, No. 15, pp. 5393–5397, 1977.
Keutmann, Henry T., et al., *Biochem. Biophys. Res. Commun.*, vol. 90, No. 3, pp. 842–848, 1979.
Kourides, Ione A., et., *Recent Progress in Hormone Research*, vol. 40, pp. 79–120, 1984.
Maniatis et al., Molecular Cloning : A Laboratory Manual, Cold Springs Harbor Literature, pp. 270–247, 1982.
Maurer et al., *J. Biol. Chem.* 259:3024–3027, 1984.
Maurer, Richard A., et al., *J. Biol. Chem.*, vol. 259, No. 8, pp. 5024–5027, 1983.
Morgan, Francis, J., et al., *J. Bio. Chem.*, vol. 20, No. 13, pp. 5247–5248, 1975.
Pierce, John G., *Endocrinology*, vol. 89, pp. 1331–1344, 1971.
Pierce, John G. and Parsons, Thomas F., *Ann. Rev. Biochem.*, vol. 50, pp. 465–495, 1981.
Policastro, Paul, et al., *J. Biol. Chem.*, vol. 258, No. 19, pp. 11492–11499, 1983.
Sairam et al. Can. J. Biochemistry 55: 755–760, 1977.
Suggs et al. *Proc. Nat'l Acad,. Sci.* 78: 6613–7. 1981.
Vamkapoulos et al., *Proc. Nat'l Acad. Sci.* 77; 3149–53, 1980.

*Primary Examiner*—David Guzo
*Attorney, Agent, or Firm*—John P. White; Cooper & Dunham LLP

[57] ABSTRACT

The gene expressing the β subunit of human thyroid stimulating hormone has been isolated. The gene has been incorporated into plasmid pBR322. Vectors can be used to transform cells which in turn produce pure β subunits. The β subunits can then be combined with the alpha subunit of human glycoprotein hormones to produce pure thyroid stimulating hormone.

9 Claims, 4 Drawing Sheets

FIG. 2A

```
CTTTTTCTTGGTTCTTTGCCCTTTCTGATTTTAACAAATAGGTTCTTTAATTTATCTTTGATTTAGC
                                    -10
    met thr ala leu phe leu met ser met leu phe gly leu ala cys gly gln ala
    ATG ACT GCT CTC TTT CTG ATG TCC ATG CTT TTT GGC CTT GCA TGT GGG CAA GCG
    -20
                          1                                         10
met ser phe cys ile pro thr glu tyr thr met his ile glu arg arg glu cys
ATG TCT TTT TGT ATT CCA ACT GAG TAT ACA ATG CAC ATC GAA AGG AGA GAG TGT 30
ala tyr cys leu thr thr ile asn thr thr ile cys ala gly tyr cys met thr arg
GCT TAT TGC CTA ACC ATC AAC ACC ACC ATC TGT GCT GGA TAT TGT ATG ACA CGG
                 20

GTATGTAGTTCATGTCACTTCTTTTGGCTGTAAATTATATAAGCCCTGAAGAAGTCCATTCCTATATAGAA

AGGAAATGAAATAAATCACAA - - - - - - - - - - - - 150-200 bp -

- - - - - - - - - - - - - AATTCAACGTGGTTAAGTTGGT

ATTGGAGAATGGGGCTAAGCAATTCTTTCGCAGTTGTATTTGTGATGAAGGAATATAAGTGAATTTATTTT
```

FIG. 2B

```
TATGTTTCTATTATCTATATGTTTCCTAAAGTCCTCACATTATGCTCTCTTTTCTGTTCTTCCCAG 35                    40                     50
asp ile asn gly lys leu phe leu pro lys tyr ala leu ser gln asp val cys
GAT ATC AAT GGC AAA CTG TTT CTT CCC AAA TAT GCT CTG TCC CAG GAT GTT TGC 60                                      70
thr tyr arg asp phe ile tyr arg thr val glu ile pro gly cys pro leu his
ACA TAT AGA GAC TTC ATC TAC AGG ACT GTA GAA ATA CCA GGA TGC CCA CTC CAT 80
val ala pro tyr phe ser tyr pro val ala leu ser cys lys cys gly lys cys
GTT GCT CCC TAT TTT TCC TAT CCT GTT GCT TTA AGC TGT AAG TGT GGC AAG TGC 90                              100
asn thr asp tyr ser asp cys ile his glu ala ile lys thr asn tyr cys thr
AAT ACT GAC TAT AGT GAC TGC ATA CAT GAA GCC ATC AAG ACA AAC TAC TGT ACC 110                       118
lys pro gln lys ser tyr leu val gly phe ser val OC
AAA CCT CAG AAG TCT TAT CTG GTA GGA TTT TCT GTC TAA TAGTGATATAATTGCAAT

TTGGTTAAATGTGCTTGCCTGAAATAAAGCTAATAAAATATTATGTTTCACATTATCTTCTGTTCATTTT

GAG
```

3

ISOLATION OF A GENE ENCODING HUMAN THYROTROPIN β SUBUNIT

This application claims benefit as a combination of U.S. Ser. No. 08/006,208, filed Jan. 19, 1993, now U.S. Pat. No. 5,840,566, which is a continuation of U.S. Ser. No. 07/671,134, filed Mar. 18, 1991, abandoned, which is a continuation of U.S. Ser. No. 06/808,004, filed Dec. 11, 1985, abandoned. The contents on the above application are incorporated into this application by reference.

FIELD OF THE INVENTION

This invention relates to the human thyroid stimulating hormone β chain or subunit (hTSH-β), and the gene producing it. Further, the invention relates to applications of this gene.

BACKGROUND AND PRIOR ART

The thyroid stimulating hormone (TSH) is a member of a family of glycoprotein hormones which includes the gonadotropins, luteinizing hormone, follicle stimulating hormone, and chorionic gonadotropin. See, e.g., Kourides et. al., Rec. Prog. Hormone Res. 40:79–120 (1984).

Each of the hormones listed supra has been found to consist of two dissimilar, noncovalently bound subunits, alpha and β.

In an individual species, the alpha subunit for all of the hormones listed has been found to be identical, while the β unit is different. It is the β subunit that gives biologic and immunologic specificity to the hormones. Again, in the same species, there are areas of strong homology among the β subunits.

Pierce, Endocrinology 89:1331 (1971), and Pierce et. al., Ann. Rev. Biochem. 50:465 (1981), show that any alpha subunit can be combined with a β subunit to give a complete hormone. Shome, et. al., J. Clin. Endocrin. Metab. 36:618 (1983); Morgan, et. al., J. Biol. Chem. 250:5247 (1975); Birken, et. al., J. Biol. Chem. 252:5386 (1977) and Keutmann, et. al., J. Biol. Chem. 252:5393 (1977), and Biochem. Biophys. Res. Commun. 90:842 (1979), have shown that the β subunits of chorionic gonadotropin and luteinizing hormone are most closely related, with amino acid sequence homology of 82%. Other β subunits have lower amino acid sequence homolgies, in the range of 25–40%. Pierce, et. al., (1981) supra.

A single gene coding for the alpha subunit of human glycoprotein hormones has been isolated. Fiddes, et. al., J. Mol. Appl. Genet. 1:3 (1981); Boothby, et. al., J. Biol. Chem. 256:5121 (1981). Additionally, seven human chorionic gonadotropin β subunit genes and one human luteinizing hormone β subunit gene have been isolated. Talmadge, et. al., DNA 2:281 (1983); Policastro, et. al., J. Biol. Chem. 258:11492 (1983). These β subunit genes are all highly homologous and are linked on a fragment of human chromosome 19, less than 50 kilobases long.

With respect to the β subunit of human thyroid stimulating hormone, it has not been possible, until now, to obtain the gene expressing this subunit. This is in spite of the fact that mouse TSH-β subunit cDNA has been synthesized and cloned and the mouse gene isolated. The gene obtained has been characterized following cross-species hybridization experiments. Gurr, et. al., Proc. Natl. Acad. Sci. 80:2122 (1983); Kourides, et. al., supra (1984). Rat and bovine TSH β subunit cDNA have also been cloned. Croyle, et al., DNA 3:231 (1984); Maurer, et. al., J. Biol. Chem. 259:5024 (1984). Now, using mouse and bovine cDNA which have been cloned, the gene expressing human thyroid stimulating hormone β chains has been obtained.

Usually, in obtaining a desired gene, the practice is to isolate the mRNA produced by transcription of the desired gene. Once this is obtained, cDNA can be synthesized and used as a hybridization probe to isolate the complementary gene. The methods for doing this are well known to the art. In the case of the β subunit of human TSH, this method has proven to be unworkable. Undegraded mRNA has not been available from human pituitary glands, post mortem or post surgery.

The difficulties involved, however, have now been overcome. By relying on cDNA of different species, i.e., mouse and bovine, it has been and now is possible to obtain the gene expressing the β subunit of human thyroid stimulating hormone.

BRIEF DESCRIPTION OF THE FIGURES

FIGS. 2A and 2B is the nucleotide sequence of protein coding exons of hTSH-β, and the amino acid sequence deduced therefrom.

DETAILED DESCRIPTION OF PREFERRED EMBODIMENTS

A human genomic library, obtained by partial digestion of white blood cell DNA with the restriction endonuclease EcoRI, followed by insertion of the partially digested genome into phage λCharon 4A was used. This library was screened using probes consisting of plasmids containing cDNA for bovine and murine TSH-β. See, Benton, et. al., Science 196:180 (1977), for the method used. The plasmid probes had been labelled with [$\alpha^{32}$P]-dCTP, via nick translation, according to the method of Rigby, et. al., J. Mol. Biol. 113:237 (1977).

Figure 1:
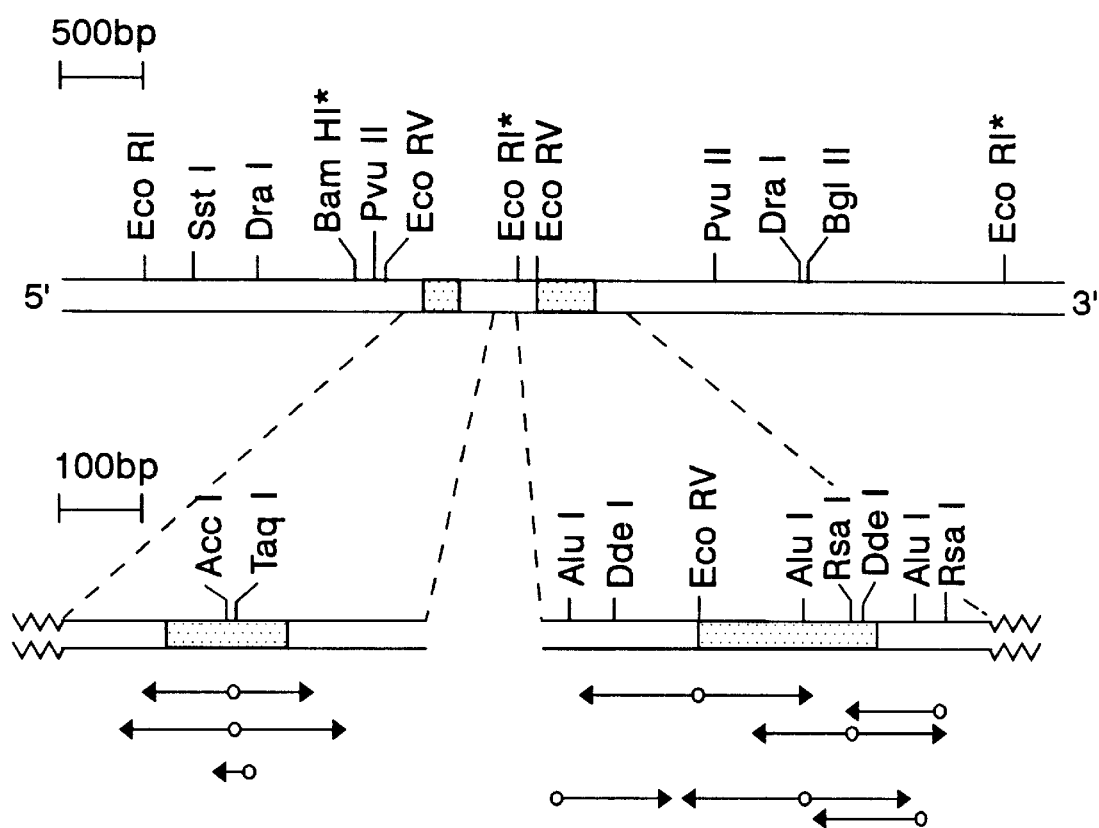
FIG. 1 is a map of the restriction enzyme sites of cloned hTSH-β.

The screening procedure described by Benton & Davis was used to examine $3 \times 10^5$ phage and yielded 3 phage which hybridized to the mouse and bovine cDNAs. The 3 phage were similar and the restriction map is presented in FIG. 1.

Two digested, hybridizing fragments were subcloned into plasmid pBR322, and the new plasmids were used to transform E. coli strain HB101. Hanahan J. Mol. Biol. 166:557 (1983). The fragments measured 0.9 Kb (BamHI-EcoRI) and 3.6 Kb (EcoRI). These fragments are adjacent, and are indicated by asterisks in FIG. 1. These fragments were themselves mapped and partially sequenced. Maxam et al, Methods Enzymol. 65:499 (1980). The determined nucleotide sequence yielded a deduced amino acid sequence which unambiguously identified the gene as expressing human TSH-β.

The plasmids and transformed E. coli cells have been deposited at the Sloan Kettering Institute for Cancer Research, and are available to one determined by the Commissioner to be entitled to these. Further, these plasmids and cell lines will be deposited with a public depository before their patent issues.

FIGS. 2A and 2B displays the nucleotide sequence of both the 0.9 and 3.6 Kb regions, together with the amino acid sequence for which these code. It will be seen that the 0.9 Kb region contains an exon encoding expresses a 20 amino acid hydrophobic signal followed by 34 amino acids of secretory TSH-β. The 3.6 Kb fragment contained an exon expressing the remaining 84 amino acids of TSH-β. Separating the two exons was an intron of about 400–450 base pairs.

Figure 3:
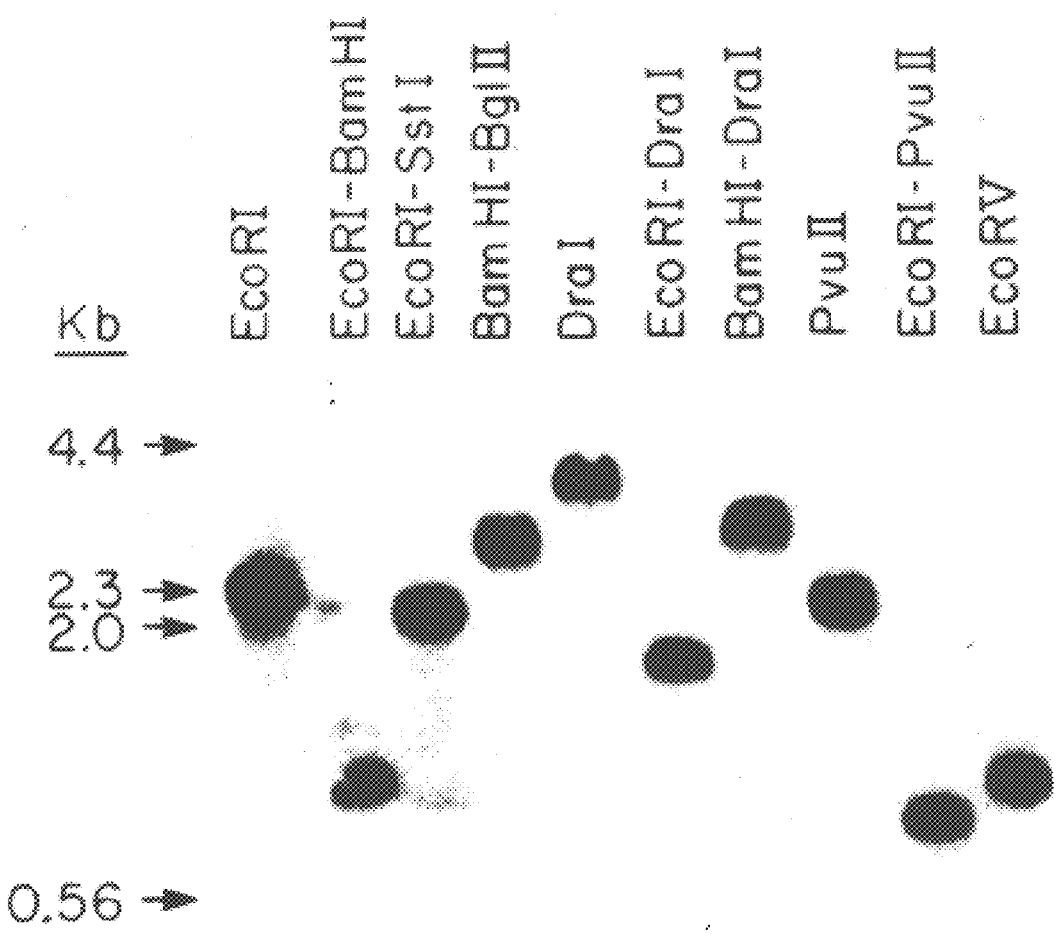
FIG. 3 shows the results of restriction analysis of hTSH-B gene in human genomic DNA.

The BamHI-EcoRI 0.9 Kb fragment was used as a probe to investigate the structure of the human TSH-β gene in total genomic DNA. The results of these experiments are displayed in FIG. 3. Briefly, samples of endonuclease digested term placental DNA were resolved on a 1% agarose gel, and then transferred to nitrocellulose filters by the method of Southern, *J. Mol. Biol.,* 98:503 (1975). Following transfer, a $^{32}$P labelled probe, comprising the 0.9 Kb fragment, was added to the filter bound DNA. Each digest of the human DNA yielded only a single hybridizing band whose size agreed with that obtained from the phage. From this, it may be concluded that human TSH-β is expressed by one gene. See FIG. 3.

The amino acid sequence deduced from the nucleotide sequence agrees with the published sequence of human TSH-β gene, with exceptions as follows: residue 8 and 9 are found to be threonine-methionine, a transposition compared to Sairam, et. al., *Can. J. Biochem.* 55:755 (1977); residue 89 is aspargine, as compared to aspartate in Sairam. Also, the derived sequence described herein contains 6 additional amino acids at the C-terminus as compared to the published sequence.

The human gene for TSH-β subunit codes for a peptide of 118 amino acids, plus an N-terminal leader sequence of 20 amino acids. The 20 amino acid leader sequence is characteristic of β-subunits of the glycoprotein hormones. See, e.g., Talmadge, et. al., *Nature* 307:37 (1984); Jameson, et. al., *J. Biol. Chem.* 259:15474 (1984). The number of amino acids in the peptide (118) is identical to the number found in mouse, rat and cow TSH-β subunits. When compared to corresponding regions of mouse, bovine, and rat TSH cDNA as presented by Gurr, et. al., *Proc. Natl. Acad; Sci.* 80:2122 (1983); Croyle, et. al., *DNA* 3:231 (1984) and Maurer, et. al., *J. Biol. Chem.* 259:5024 (1984), the protein encoding regions of the human gene display homology of 84%, 90%, and 83%, respectively.

Study of this gene reveals that the intron occurs between amino acids 34 and 35 of the secretory protein. This is a conserved position for the 3'-ward introns occurring also in human and rat luteinizing hormone β subunits, Talmadge, et. al., supra (1984); Jameson, et. al., supra (1984).

Due to the difficulties in obtaining undegraded human TSH-β mRNA, it was difficult to identify 5' and 3' untranslated regions of the gene. It is known that the sequence immediately downstream of the stop codon is strongly homologous to 3'-untranslated regions of mouse, bovine and rat TSH-β cDNAs. It is therefore likely that the 3' untranslated region is present in the clone. In contrast, sequences upstream from the first methionine codon bear no homology to the 5'-untranslated regions of other species. This lends support to the hypothesis that this region is an intron.

While the embodiment set forth supra, describes plasmids prepared using pBR322, one skilled in the art will appreciate that there are many plasmids which can be used in subcloning. These plasmids may be naturally occurring or synthesized in the laboratory.

Further, one skilled in the art will appreciate the applicability of this invention to the transformation of cells, both prokaryotic and eukaryotic. As has been described, supra, *E. coli* strain HB101 was transformed by plasmid pBR322 which has been subcloned with fragments of the human TSH-β gene. Using similar mechanisms, *E. coli* and other prokaryotes may be so transformed.

Additionally, the state of the art is such that eukaryotic cells may be transformed by appropriate vectors such as viruses containing the human TSH-β gene. This allows for production of this protein, in glycosylated form, in vitro. By amplification means known to the art, it is also possible to increase the production of the protein to high levels.

Perhaps the most interesting use of the isolated gene is in diagnostics. Various endocrine disorders are characterized by overproduction or underproduction of hormones, including thyroid stimulating hormone. One could administer hTSH made by recombinant DNA technology to humans in order to determine whether thyroid gland failure is due to primary thyroid disease or central pituitary or hypothalamic disease.

The terms and expressions which have been employed are used as terms of description and not of limitation, and there is no intention in the use of such terms and expressions of excluding any equivalents of the features shown and described or portions thereof; it being recognized that various modifications are possible within the scope of the invention.

What is claimed is:

1. A method for producing the β subunit of human thyroid stimulating hormone comprising:

(a) transforming cells with a vector containing DNA encoding the β subunit of human thyroid stimulating hormone and culturing said cells under conditions suitable for expression of the β subunit of human thyroid stimulating hormone; and (b) recovering the β subunit of human thyroid stimulating hormone so produced.

2. The method of claim 1, wherein the DNA comprises the below sequence:

```
ATG ACT GCT CTC TTT CTG ATG TCC ATG CTT

TTT GGC CTT GCA TGT GGG CAA GCG ATG TCT

TTT TGT ATT CCA ACT GAG TAT ACA ATG CAC

ATC GAA AGG AGA GAG TGT GCT TAT TGC CTA

ACC ATC AAC ACC ACC ATC TGT GCT GGA TAT

TGT ATG ACA CGG followed by a sequence of about 400–450
nucleotides, and ending with the sequence:

GAT ATC AAT GGC AAA CTG TTT CTT CCC AAA

TAT GCT CTG TCC CAG GAT GTT TGC ACA TAT

AGA GAC TTC ATC TAC AGG ACT GTA GAA ATA

CCA GGA TGC CCA CTC CAT GTT GCT CCC TAT

TTT TCC TAT CCT GTT GCT TTA AGC TGT AAG

TGT GGC AAG TGC AAT ACT GAC TAT AGT GAC

TGC ATA CAT GAA GCC ATC AAG ACA AAC TAC

TGT ACC AAA CCT CAG AAG TCT TAT CTG GTA

GGA TTT TCT GTC TAA.
```

3. The method of claim 1, wherein the DNA comprises the below sequence:

```
ATG ACT GCT CTC TTT CTG ATG TCC ATG CTT

TTT GGC CTT GCA TGT GGG CAA GCG ATG TCT

TTT TGT ATT CCA ACT GAG TAT ACA ATG CAC

ATC GAA AGG AGA GAG TGT GCT TAT TGC CTA

ACC ATC AAC ACC ACC ATC TGT GCT GGA TAT

TGT ATG ACA CGG.
```

4. The method of claim 1, wherein the DNA comprises the below sequence:

```
GAT ATC AAT GGC AAA CTG TTT CTT CCC AAA

TAT GCT CTG TCC CAG GAT GTT TGC ACA TAT
```

-continued
```
AGA GAC TTC ATC TAC AGG ACT GTA GAA ATA

CCA GGA TGC CCA CTC CAT GTT GCT CCC TAT

TTT TCC TAT CCT GTT GCT TTA AGC TGT AAG

TGT GGC AAG TGC AAT ACT GAC TAT AGT GAC

TGC ATA CAT GAA GCC ATC AAG ACA AAC TAC

TGT ACC AAA CCT CAG AAG TCT TAT CTG GTA

GGA TTT TCT GTC TAA.
```

5. The method of claim 1, wherein the vector is a plasmid.

6. The method of claim 1, wherein the vector is a virus.

7. The method of claim 1, wherein the cell is a prokaryote.

8. The method of claim 1, wherein the cell is a eukaryote.

9. The method of claim 7, wherein the prokaryote is a bacterium.

\* \* \* \* \*

UNITED STATES PATENT AND TRADEMARK OFFICE
CERTIFICATE OF CORRECTION

| | |
|---|---|
| PATENT NO. | : 6,114,144 |
| APPLICATION NO. | : 08/957545 |
| DATED | : September 5, 2000 |
| INVENTOR(S) | : Ione A. Kourides and Graham Kerr Whitfield |

It is certified that error appears in the above-identified patent and that said Letters Patent is hereby corrected as shown below:

In the specification at column 1, line 3:

The invention described herein was made in the course of work under Grant No. RO1-CA-23185 from the National Institute of Health. The United States Government has certain rights in this invention.

Signed and Sealed this

Fifth Day of February, 2008

JON W. DUDAS
*Director of the United States Patent and Trademark Office*